(12) United States Patent
McComas et al.

(10) Patent No.: US 7,601,744 B2
(45) Date of Patent: Oct. 13, 2009

(54) BENZOTHIADIAZOLYLPHENYLALKYLAMINE DERIVATIVES AND METHODS OF THEIR USE

(75) Inventors: Casey Cameron McComas, Phoenixville, PA (US); Puwen Zhang, Audubon, PA (US); Eugene John Trybulski, Huntingdon Valley, PA (US); An Thien Vu, Pottstown, PA (US); Eugene Anthony Terefenko, Center Valley, PA (US)

(73) Assignee: Wyeth, Madison, NJ (US)

( * ) Notice: Subject to any disclaimer, the term of this patent is extended or adjusted under 35 U.S.C. 154(b) by 144 days.

(21) Appl. No.: 11/528,792

(22) Filed: Sep. 27, 2006

(65) Prior Publication Data
US 2007/0072918 A1 Mar. 29, 2007

Related U.S. Application Data

(60) Provisional application No. 60/721,693, filed on Sep. 29, 2005.

(51) Int. Cl.
*A61K 31/41* (2006.01)
*C07D 285/06* (2006.01)

(52) U.S. Cl. .................. 514/361; 548/127; 548/121

(58) Field of Classification Search ........... 514/361; 548/127, 121
See application file for complete search history.

(56) References Cited

FOREIGN PATENT DOCUMENTS

| WO | 99/44601 A1 | 9/1999 |
| WO | 2004/043903 A1 | 5/2004 |
| WO | 2005/037207 A2 | 4/2005 |

OTHER PUBLICATIONS

Ashton et al. Journal of Sex & Marital Therapy, vol. 23 (3), 1997, pp. 165-175, Abstract only.*
U.S. Appl. No. 11/529,441, filed Sep. 27, 2006, Mahaney et al.
U.S. Appl. No. 11/529,450, filed Sep. 27, 2006, McComas et al.
Berendsen, H. H. G., "Effect of tibolone and raloxifene on the tail temperature of oestrogen-deficient rats," *European Journal of Pharmacology*, 2001, 419(1), 47-54.
Berendsen, H. H. G., "The role of serotonin in hot flushes," *Maturitas*, 2000, 36(3), 155-164.
Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4), 285-298.
Bundgaard, H., "Means to enhance penetration; Prodrugs as a means to improve the delivery of peptide drugs," *Advanced Drug Deliver Reviews*, 1992, 8, 1-38.

Eliel, E. L., *Stereochemistry of Carbon Compounds*, McGraw Hill, NY (1962) Ch. 4, pp. 46-87.
Fink, G. et al., "Oestrogen and mental state," *Nature*, 1996, 383(6598), 306.
Freedman, R. R. et al., "Clonidine raises the sweating threshold in symptomatic but not asymptomatic postmenopausal women," *Fertility & Sterility*, 2000, 74(1), 20-3.
French, N., "α$_2$-Adrenoceptors and I$_2$ sites in the mammalian central nervous system," *Pharmacol. Ther.*, 1995, 68(2), 175-208.
Greene, T.W. and Wuts, P.G.M., *Protective Groups in Organic Synthesis* 2d. Ed., Wiley & Sons, 1991, Ch. 2 (pp. 10-142), Ch. 5 (pp. 224-276), and Ch. 7 (pp. 309-405).
Higuchi and Stella (eds.), *Prodrugs as Novel Drug Delivery Systems*, American Chemical Society (1975), pp. 1-115 and 196-223.
Hughes, David L., "Progress in the Mitsunobu Reaction. A Review," *Organic Preparations and Procedures International*, 1996, 28(2), 127-164.
Jacques, J. et al., *Enantiomers, Racemates and Resolutions*, Wiley Interscience, NY (1981) pp. 251-434.
Janowsky, D. S. et al., "Desipramine: an overview," *Journal of Clinical Psychiatry*, 1984, 45(10 Pt 2), 3-9.
Katovich, M. J. et al., "Mechanisms Mediating the Thermal Response to Morphine Withdrawal in Rats," *Proceedings of the Society for Experimental Biology & Medicine*, 1990, 193(2), 129-35.
Krämer, P. et al., "Prevention of Hot Flushes with CPA in the Hormonal Treatment of Prostatic Cancer Results of a Placebo-Controlled Double-Blind Trial," *3rd Int'l Symposium on Recent Advances in Urological Cancer Diagnosis and Treatment-Proceedings*, Paris, France: SCI, 3-7 1992.

(Continued)

*Primary Examiner*—Yong Chu
(74) *Attorney, Agent, or Firm*—Doina G. Ene; A. David Joran; David R. Kurlandsky

(57) ABSTRACT

The present invention is directed to benzothiadiazolylphenylalkylamine derivatives of formula I:

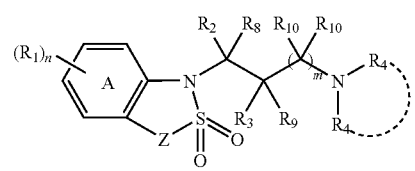

or a pharmaceutically acceptable salt thereof, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

41 Claims, 2 Drawing Sheets

OTHER PUBLICATIONS

Krogsgaard-Larsen, et al., (ed). *Design and Application of Prodrugs, Textbook of Drug Design and Development*, Chapter 5, 113-191, 1991.

Kronenberg, F. et al., "Thermoregulatory Physiology of Menopausal Hot Flashes: A Review," *Can. J. Physiol. Pharmacol.*, 1987, 65, 1312-1324.

Loprinzi, C.L. et al., "Venlafaxine in management of hot flashes in survivors of breast cancer: a randomized controlled trial," *Lancet*, Dec. 16, 2000, 356(9247), 2059-2063.

Mackinnon et al., "α2-Adrenoceptors: more subtypes but fewer functional differences," *TIPS*, 1994, 15, 119-123.

Merchenthaler et al., "The effect of estrogens and antiestrogens in a rat model for hot flush," *Maturitas*, 1998, 30(3), 307-316.

Pacholczyk, T. et al., "Expression cloning of a cocaine-and antidepressant-sensitive human noradrenaline transporter," *Nature*, 1991, 350(6316), 350-354.

Panek, D.U. et al., "Effect of continuous intraventricular estrogen or catechol estrogen treatment on catecholamine turnover in various brain regions," *J. Pharmacol. Exp. Ther.*, 1986, 236(3), 646-652.

Prasad, P.D., et al., "Functional expression of the plasma membrane serotonin transporter but not the vesicular monoamine transporter in human placental trophoblasts and choriocarcinoma cells," *Placenta*, 1996, 17(4), 201-7.

*Remington's Pharmaceutical Sciences*, 17th Ed., Gennaro, A. R. (Ed.), Mack Publishing Company, Easton, PA (1985) pp. 1409-1677.

Sharpless, et. al., "Asymmetric Epoxidation of Allyl Alcohol: Efficient Routes to Homochiral β-Adrenergic Blocking Agents," *J. Org. Chem.* 1986, 51, 3710-3712.

Stearns,V. et al., "Paroxetine controlled release in the treatment of menopausal hot flashes," *JAMA*, 2003, 289:2827-2834.

Waldinger et al., "Treatment of hot flushes with mirtazapine: four case reports," *Maturitas*, 2000, 36(3), 165-168.

Widder, et al. (ed.), *Methods in Enzymology*, vol. 112, Academic Press (1985), pp. 309-323.

Wilen, S.H. *Tables of Resolving Agents and Optical Resolutions*, pp. 268-298, E.L. Eliel, Ed., University of Notre Dame Press, Notre Dame, IN 1972.

Wilen, S.H., et al., "Strategies in optical resolutions," *Tetrahedron*, 33, 2725-2736, 1977.

* cited by examiner

BENZOTHIADIAZOLYLPHENYLALKYLAMINE DERIVATIVES AND METHODS OF THEIR USE

CROSS REFERENCE TO RELATED APPLICATIONS

This application claims priority to U.S. Application No. 60/721,693 filed Sep. 29, 2005, the entire disclosure of which is incorporated herein by reference.

FIELD OF THE INVENTION

The present invention relates to benzothiadiazolylphenylalkylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., $3^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg, et al., "Thermoregulatory Physiology of Menopausal Hot Flashes: A Review," Can. J. Physiol. Pharmacol., 1987, 65:1312-1324).

The fact that estrogen treatment (e.g., estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_{\alpha 2}$ receptors, i.e., are $\alpha_{2A}$, $\alpha_{2B}$, $\alpha_{2C}$ and $\alpha_{2D}$ (Mackinnon et al., TIPS, 1994, 15: 119; French, Pharmacol. Ther., 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine,* 1990, 193(2): 129-35, Freedman et al., *Fertility & Sterility,* 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to benzothiadiazolylphenylalkylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the invention is directed to compounds of formula I:

$$\text{(structure I: benzothiadiazolyl-phenyl group with }(R_1)_n\text{ on ring A, substituents }R_2, R_8, R_{10}, R_{10}, R_3, R_9, R_4, R_4\text{ and Z=S(=O)_2)}$$

or a pharmaceutically acceptable salt thereof;

wherein:

Z is $CR_5R_6$, or $NR_7$;

$R_1$ is, independently at each occurrence, alkyl, alkoxy, halo, $CF_3$, $OCF_3$, arylalkoxy substituted with 0 to 3 $R_{11}$, aryloxy substituted with 0 to 3 $R_{11}$, aryl substituted with 0 to 3 $R_{11}$, heteroaryl substituted with 0 to 3 $R_{11}$, hydroxy, alkanoyloxy, nitro, cyano, alkenyl, alkynyl, alkylsulfoxide, arylsulfoxide substituted with 0 to 3 $R_{11}$, alkylsulfone, arylsulfone substituted with 0 to 3 $R_{11}$, alkylsulfonamide, arylsulfonamide substituted with 0 to 3 $R_{11}$, heteroaryloxy substituted with 0 to 3 $R_{11}$, heteroarylmethoxy substituted with 0-3 $R_{11}$, alkylamido, or arylamido substituted with 0 to 3 $R_{11}$; or two adjacent $R_1$ represent methylenedioxy;

$R_2$ is aryl substituted with 0 to 3 $R_1$, or heteroaryl substituted with 0 to 3 $R_1$;

$R_3$ is H, F, $C_1$ to $C_4$ alkyl, or $OR_{12}$;

$R_{12}$ is H or $C_1$ to $C_4$ alkyl;

$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$ to $C_4$ alkyl, F, or $CF_3$;

$R_5$ and $R_6$ are, independently at each occurrence, H, $C_1$ to $C_4$ alkyl, alkenyl, alkynyl, alkoxy, aryl substituted with 0 to 3 $R_1$, heteroaryl substituted with 0 to 3 $R_1$, or cyano; or $R_5$ and $R_6$, together with the carbon through which they are attached, form a carbocyclic ring of 3 to 7 carbon atoms where 1 to 3 carbon atoms may be optionally replaced with N, O, S, or $SO_2$, and where any carbon ring atom or additional N atom may be optionally substituted with $C_1$ to $C_4$ alkyl, F, or $CF_3$;

$R_7$ is H, $C_1$ to $C_6$ alkyl, alkenyl, alkynyl, $C_3$ to $C_6$ cycloalkyl, aryl substituted with 0 to 3 $R_1$, or heteroaryl substituted with 0 to 3 $R_1$;

$R_8$ is H or $C_1$ to $C_4$ alkyl;

$R_9$ is H, F, or $C_1$ to $C_4$ alkyl;

$R_{10}$ is, independently at each occurrence, H, or $C_1$ to $C_4$ alkyl; or $R_{10}$ and $R_4$, together with the nitrogen to which $R_4$ is attached, form a nitrogen-containing ring containing 3 to 6 carbon atoms;

n is an integer from 0 to 4;

m is an integer from 1 to 2;

$R_{11}$ is alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido; or two adjacent $R_{11}$ also represent methylenedioxy;

wherein 1 to 3 carbon atoms in ring A may optionally be replaced with N; and wherein the dotted line between the two $R_4$ groups represents an optional heterocyclic ring of 4 to 6 ring atoms that may be formed between the two $R_4$ groups, together with the nitrogen through which they are attached.

In yet other embodiments, the present invention is directed to compositions, comprising:

a. at least one compound of formula I; and b. at least one pharmaceutically acceptable carrier.

In another embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:

administering to said subject an effective amount of at least one compound of formula I or pharmaceutically acceptable salt thereof.

In yet another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In further embodiments, the present invention is directed to methods for treating or preventing pain in a subject in need thereof, comprising the step of:
administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:
administering to said subject an effective amount of at least one compound of formula I or pharmaceutically acceptable salt thereof.

In another embodiment, the present invention is directed to methods for treating or preventing chronic fatigue syndrome in a subject in need thereof, comprising the step of:
administering to said subject an effective amount of at least one compound of formula I or pharmaceutically acceptable salt thereof.

In another embodiment, the present invention is directed to methods for treating or preventing fibromylagia syndrome in a subject in need thereof, comprising the step of:
administering to said subject an effective amount of at least one compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
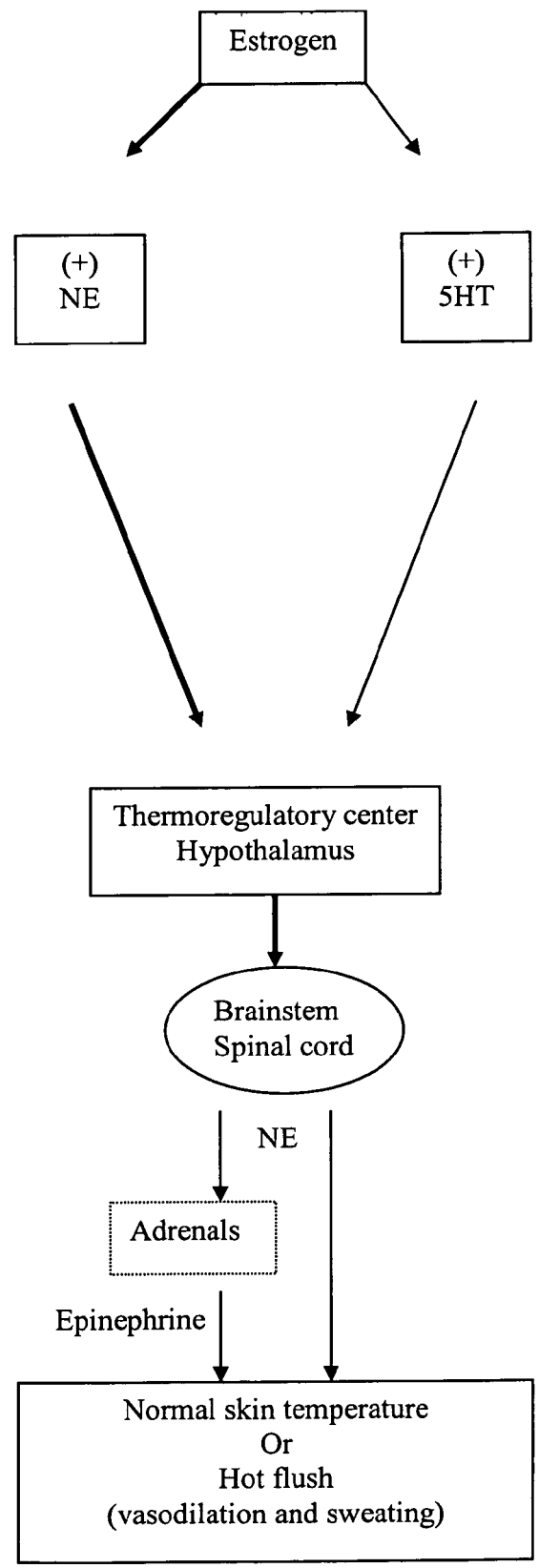
FIG. 1 is an overview of estrogen action on norepinephrine/serotonin mediated thermoregulation.

The present invention is directed to benzothiadiazolylphenylalkylamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "$ED_{50}$ value" means dose which results in 50% alleviation of the observed condition or effect (50% mean maximum endpoint).

"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I, or a pharmaceutically acceptable salt thereof, may be administered, preferably, at a dosage of from about 0.1 mg/day to about 500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

The term "side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

"Heteroalkyl," as used herein, refers to a substituent of the general formula (alkyl-X)$_n$-alkyl-, where each "alkyl" is independently as defined above, "X" is a sulfur, oxygen, or N heteroatom-containing moiety, and n is 1-4, preferably one. Heteroalkyl groups include, but are not limited to, methoxymethyl, ethoxyethyl, methoxyethyl, methylsulfanylmethyl, ethylsulfanylethyl, methylsulfanylethyl, methylaminoethyl, ethylaminoethyl, and methylaminoethyl.

"Alkenyl," as used herein, refers to an alkyl group of at least two carbon atoms having one or more double bonds, wherein alkyl is as defined herein. Alkenyl groups can be optionally substituted. The alkenyl group is suitably a $C_2$-$C_{20}$ alkenyl, preferably. a $C_2$-$C_8$ alkenyl or a $C_2$-$C_6$ alkenyl, e.g. a $C_2$-$C_4$ alkenyl.

"Alkynyl," as used herein, refers to an alkyl group of at least two carbon atoms having one or more triple bonds, wherein alkyl is as defined herein. Alkynyl groups can be optionally substituted. The alkynyl group is suitably a $C_2$-$C_{20}$ alkynyl, preferably. a $C_2$-$C_8$ alkynyl or a $C_2$-$C_6$ alkynyl, e.g. a $C_2$-$C_4$ alkynyl.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 heteroatom ring members selected from sulfur, oxygen and nitrogen. Heteroaryl groups can have, for example, from about 3 to about 50 carbon atoms (and all combinations and subcombinations of ranges and specific numbers of carbon atoms therein), with from about 4 to about 10 carbons being preferred. Heteroaryl may for example be a 5 to 14 ring membered group having 4 to 10 carbon atoms and 1 to 4 heteroatoms selected from sulfur, oxygen and nitrogen. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinyl. Also included are fused ring and spiro compounds containing, for example, the above heterocycles.

"Alkoxy," as used herein, refers to the group R—O— where R is an alkyl group as defined herein.

"Aryloxy," as used herein, refers to the group R—O— where R is an aryl group, as defined herein.

"Heteroaryloxy," as used herein, refers to the group R—O— where R is a heteroaryl group, as defined herein.

"Heteroarylmethyl" as used herein, refers to the group R—$CH_2$— where R is a heteroaryl group, as defined herein.

"Heteroarylmethoxy," as used herein, refers to the group R—$CH_2$—O— where R is a heteroaryl group, as defined herein.

"Arylalkoxy," as used herein, refers to the group $R_z$—$R_x$—O— where $R_z$ is an aryl group and $R_x$ is an alkyl group, as defined herein.

"Alkanoyloxy," as used herein, refers to the group R—C(=O)—O— where R is an alkyl group of 1 to 5 carbon atoms.

"Arylalkyl" as used herein, refers to the group $R_z$—$R_y$— where $R_z$ is an aryl group, as defined herein, and where $R_y$ is an alkyl group, as defined herein.

"Alkylsulfoxide," as used herein, refers to as used herein, refers to —S(=O)—R, where R is alkyl, as defined above.

"Alkylsulfone," as used herein, refers to —S(=O)$_2$—R, where R is alkyl, as defined above.

"Arylsulfoxide," as used herein, refers to as used herein, refers to —S(=O)—R, where R is aryl, as defined above.

"Arylsulfone," as used herein, refers to —S(=O)$_2$—R, where R is aryl, as defined above.

"Alkylsulfonamide," as used herein, refers to —NR—S(=O)$_2$—R, where each R is independently, alkyl, as defined above or the NR part may also be NH.

"Arylsulfonamide," as used herein, refers to —NR—S(=O)$_2$—R, where each R is independently, aryl, as defined above or the NR part may also be NH (provided that the other R is aryl).

"Heteroarylmethoxy," as used herein, refers to —O$CH_2$—R, where R is heteroaryl, as defined above.

"Alkylamido," as used herein, refers to —NR—C(=O)—R, where each R is independently, alkyl, as defined above, or the NR part may also be NH.

"Arylamido," as used herein, refers to —N$R_y$—C(=O)—$R_z$, where $R_y$ and $R_z$ are H or aryl (provided that at least one of $R_y$ and $R_z$ is aryl), as defined above.

"Halo," as used herein, refers to chloro, bromo, fluoro, and iodo.

When any variable occurs more than one time in any constituent or any formula, its definition in each occurrence is independent of its definition at every other occurrence. Combinations of substituents and/or variables and/or replacements atoms or groups are permissible only if such combinations result in a stable compound.

In one embodiment, the invention is directed to compounds of formula I:

$$\text{(R}_1\text{)}_n\text{—A—N(R}_2\text{)(R}_8\text{)—C(R}_3\text{)—C(R}_{10}\text{)}_m\text{—N(R}_4\text{)(R}_4\text{)}$$
with Z—S(=O)$_2$ bridge and R$_9$, as depicted or a pharmaceutically acceptable salt thereof;
wherein:
Z is $CR_5R_6$, or $NR_7$;
$R_1$ is, independently at each occurrence, alkyl, alkoxy, halo, $CF_3$, $OCF_3$, arylalkoxy substituted with 0 to 3 $R_{11}$, aryloxy substituted with 0 to 3 $R_{11}$, aryl substituted with 0 to 3 $R_{11}$, heteroaryl substituted with 0 to 3 $R_{11}$, hydroxy, alkanoyloxy, nitro, cyano, alkenyl, alkynyl, alkylsulfoxide, arylsulfoxide substituted with 0 to 3 $R_{11}$, alkylsulfone, arylsulfone substituted with 0 to 3 $R_{11}$, alkylsulfonamide, arylsulfonamide substituted with 0 to 3 $R_{11}$, heteroaryloxy substituted with 0 to 3 $R_{11}$, heteroarylmethoxy substituted with 0-3 $R_{11}$, alkylamido, or arylamido substituted with 0 to 3 $R_{11}$; or two adjacent $R_1$ represent methylenedioxy;
$R_2$ is aryl substituted with 0 to 3 $R_1$, or heteroaryl substituted with 0 to 3 $R_1$;
$R_3$ is H, F, $C_1$ to $C_4$ alkyl, or $OR_{12}$;
$R_{12}$ is H or $C_1$ to $C_4$ alkyl;
$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, or
both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$ to $C_4$ alkyl, F, or $CF_3$;
$R_5$ and $R_6$ are, independently at each occurrence, H, $C_1$ to $C_4$ alkyl, alkenyl, alkynyl, alkoxy, aryl substituted with 0 to 3 $R_1$, heteroaryl substituted with 0 to 3 $R_1$, or cyano; or
$R_5$ and $R_6$, together with the carbon through which they are attached, form a carbocyclic ring of 3 to 7 carbon atoms where 1 to 3 carbon atoms may be optionally replaced with N, O, S, or $SO_2$, and where any carbon ring atom or additional N atom may be optionally substituted with $C_1$ to $C_4$ alkyl, F, or $CF_3$;
$R_7$ is H, $C_1$ to $C_6$ alkyl, alkenyl, alkynyl, $C_3$ to $C_6$ cycloalkyl, aryl substituted with 0 to 3 $R_1$, or heteroaryl substituted with 0 to 3 $R_1$;
$R_8$ is H or $C_1$ to $C_4$ alkyl;
$R_9$ is H, F, or $C_1$ to $C_4$ alkyl;
$R_{10}$ is, independently at each occurrence, H, or $C_1$ to $C_4$ alkyl; or $R_{10}$ and $R_4$, together with the nitrogen to which $R_4$ is attached, form a nitrogen-containing ring containing 3 to 6 carbon atoms;
n is an integer from 0 to 4;
m is an integer from 1 to 2;
$R_{11}$ is alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido; or two adjacent $R_{11}$ also represent methylenedioxy;
wherein 1 to 3 carbon atoms in ring A may optionally be replaced with N; and
wherein the dotted line between the two $R_4$ groups represents an optional heterocyclic ring of 4 to 6 ring atoms that may be formed between the two $R_4$ groups, together with the nitrogen through which they are attached.

In certain preferred embodiments of compounds of formula I,
Z is $CR_5R_6$;
$R_5$ and $R_6$ are, independently at each occurrence, $C_1$ to $C_4$ alkyl, or
$R_5$ and $R_6$, together with the carbon through which they are attached, form a carbocyclic ring of 3 to 7 carbon atoms where any carbon ring atom may be optionally substituted with F or $CF_3$;
$R_1$ is, independently at each occurrence, methyl, methoxy, hydroxy, halo, CN, $CF_3$, or $OCF_3$,
$R_2$ is aryl substituted with 0 to 2 $R_1$, or heteroaryl substituted with 0 to 2 $R_1$;
$R_3$ is H or OH;
one of $R_4$ is methyl and the other $R_4$ is H;
$R_8$ is H;
$R_9$ is H;
$R_{10}$ is H;
m is 1,
n is 0 to 2; and
no carbon atoms in the ring A are replaced with N.

In certain other preferred embodiments of compounds of formula I,
Z is $NR_7$;
$R_7$ is $C_1$ to $C_4$ alkyl, or aryl substituted with 0 to 2 $R_1$;
$R_1$ is, independently at each occurrence, methyl, methoxy, hydroxy, halo, CN, $CF_3$, or $OCF_3$,
$R_2$ is aryl substituted with 0 to 2 $R_1$, or heteroaryl substituted with 0 to 2 $R_1$;
$R_3$ is H or OH;
one of $R_4$ is methyl and the other $R_4$ is H;
$R_8$ is H;
$R_9$ is H;
$R_{10}$ is H;
m is 1;
n is 0 to 2 and
no carbon atoms in the ring A are replaced with N.

In certain preferred embodiments of compounds of formula I, Z is $CR_5R_6$, especially $CH_2$.

In certain preferred embodiments of compounds of formula I, Z is $NR_7$, especially NH.

In certain preferred embodiments of compounds of formula I, $R_1$ is, independently at each occurrence, alkyl, alkoxy, halo, $CF_3$, $OCF_3$, arylalkoxy, aryloxy, aryl, heteroaryl, hydroxy, alkanoyloxy, nitro, cyano, alkenyl, alkynyl, alkylsulfoxide, arylsulfoxide, alkylsulfone, arylsulfone, alkylsulfonamide, arylsulfonamide, heteroaryloxy, heteroarylmethoxy, or arylamido, especially alkyl, alkoxy, halo, $CF_3$, $OCF_3$, arylalkoxy, aryloxy, aryl, heteroaryl, heteroaryloxy, hydroxy, alkanoyloxy, nitro, cyano, alkenyl, and alkynyl. In certain more preferred embodiments of formula I, $R_1$ is alkyl, alkoxy, halo, $CF_3$, $OCF_3$, aryl, heteroaryl, hydroxy, alkanoyloxy, nitro, and cyano. In certain even more preferred embodiments of formula I, $R_1$ is alkyl (especially methyl, ethyl, propyl, and butyl), alkoxy (especially methoxy and ethoxy), halo (especially fluoro and chloro), $CF_3$, $OCF_3$, aryl (especially phenyl and naphthyl), heteroaryl (especially pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl), hydroxy, alkanoyloxy (especially aceto), nitro, and cyano. $R_1$ may suitably be methyl, methoxy, hydroxy, halo, CN, $CF_3$, or $OCF_3$.

In certain preferred embodiments of compounds of formula I, two adjacent $R_1$ represent methylenedioxy.

In certain preferred embodiments of compounds of formula I, $R_2$ is aryl substituted with 0 to 3 $R_1$. In certain especially preferred embodiments, $R_2$ is optionally substituted aryl (especially phenyl and naphthyl optionally monosubstituted or disubstituted with halo, including fluoro and chloro), such as phenyl, naphthyl, chloro-substituted phenyl, fluoro-substituted phenyl, and chloro, fluoro-substituted phenyl.

In certain preferred embodiments of compounds of formula I, $R_2$ is heteroaryl substituted with 0 to 3 $R_1$. In certain especially preferred embodiments, $R_2$ is heteroaryl (especially pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl). $R_2$ may suitably be aryl substituted with 0 to 2 $R_1$, or heteroaryl substituted with 0 to 2 $R_1$.

In certain preferred embodiments of compounds of formula I, $R_3$ is H, F, or $C_1$ to $C_4$ alkyl. In certain preferred embodiments of compounds of formula I, $R_3$ is $OR_{12}$. In certain especially preferred embodiments, $R_3$ is H, F, methyl, ethyl, hydroxy, or methoxy. $R_3$ may suitably be H or OH.

In certain preferred embodiments of compounds of formula I, $R_{12}$ is H or methyl.

In certain preferred embodiments of compounds of formula I, $R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl. In certain more preferred embodiments, $R_4$ is, independently at each occurrence, H or $C_1$ to $C_4$ alkyl (especially methyl and ethyl).

In certain preferred embodiments of compounds of formula I, both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$ to $C_4$ alkyl, F, or $CF_3$. In certain embodiments one of $R_4$ is methyl and the other $R_4$ is H.

In certain preferred embodiments of compounds of formula I, $R_5$ and $R_6$ are, independently at each occurrence, H, $C_1$ to $C_4$ alkyl, aryl, heteroaryl, or cyano. In certain more preferred embodiments, $R_5$ and $R_6$ are, independently at each occurrence, H, methyl, or ethyl.

In certain preferred embodiments of compounds of formula I, $R_5$ and $R_6$, together with the carbon through which they are attached, form a carbocyclic ring of 3 to 7 carbon atoms where 1 to 3 carbon atoms may be optionally replaced with N, O, S, or $SO_2$, and where any carbon ring atom or additional N atom may be optionally substituted with $C_1$ to $C_4$ alkyl, F, or $CF_3$. In certain embodiments $R_5$ and $R_6$, together with the carbon through which they are attached, form a carbocyclic ring of 3 to 7 carbon atoms where any carbon ring atom may be optionally substituted with F or $CF_3$.

In certain preferred embodiments of compounds of formula I, $R_7$ is H, $C_1$ to $C_6$ alkyl, $C_3$ to $C_6$ cycloalkyl, aryl (especially optionally monosubstituted with $R_1$), or heteroaryl (especially optionally monosubstituted with $R_1$). In certain more preferred embodiments, $R_7$ is H, methyl, ethyl, propyl, butyl, cyclopentyl, cyclohexyl, aryl (especially phenyl and naphthyl, both optionally monosubstituted with halo, especially chloro), or heteroaryl especially pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl). In particularly preferred embodiments, $R^7$ is H, $C_1$ to $C_4$ alkyl (such as methyl, n-propyl, isopropyl, n-butyl, t-butyl) or substituted phenyl (such as chloro-substituted phenyl and fluoro-substituted phenyl). In other especially preferred embodiments, $R^7$ is methyl, isopropyl, or chloro-substituted phenyl. In certain embodiments $R_7$ is $C_1$ to $C_4$ alkyl, or aryl substituted with 0 to 2 $R_1$.

In certain preferred embodiments of compounds of formula I, $R_8$ is H, methyl, or ethyl, especially H.

In certain preferred embodiments of compounds of formula I, $R_9$ is H, methyl, or ethyl, especially H.

In certain preferred embodiments of compounds of formula I, $R_{10}$ is, independently at each occurrence, H, methyl, or ethyl, especially H;

In certain preferred embodiments of compounds of formula I, $R_{10}$ and $R_4$, together with the nitrogen to which $R_4$ is attached, form a nitrogen-containing ring containing 3 to 6 carbon atoms.

In certain preferred embodiments of compounds of formula I, n is an integer from 0 to 2, especially 0 to 1, more especially 0.

In certain preferred embodiments of compounds of formula I, m is 1.

In certain preferred embodiments of compounds of formula I, $R_{11}$ is alkyl (especially methyl, ethyl, propyl, and butyl), alkoxy (especially methoxy and ethoxy), halo (especially fluoro and chloro), $CF_3$, $OCF_3$, hydroxy, alkanoyloxy (especially aceto), nitro, or cyano.

In certain preferred embodiments of compounds of formula I, two adjacent $R_{11}$ also represent methylenedioxy.

In certain preferred embodiments of compounds of formula I, 1 to 3 carbon atoms in ring A may optionally be replaced with N. In certain embodiments no carbon atoms in the ring A are replaced with N.

In certain preferred embodiments of compounds of formula I, the dotted line between the two $R_4$ groups represents an optional heterocyclic ring of 4 to 6 ring atoms that may be formed between the two $R_4$ groups, together with the nitrogen through which they are attached.

Preferred compounds of formula I include:
  3-[3-(4-chlorophenyl)-2,2-dioxido-2,1,3-benzothiadiazol-1(3H)-yl]-N-methyl-3-phenylpropan-1-amine;
  3-(3-chloro-5-fluorophenyl)-3-(3-isopropyl-2,2-dioxido-2,1,3-benzothiadiazol-1(3H)-yl)-N-methylpropan-1-amine;
  3-(3-chloro-5-fluorophenyl)-N-methyl-3-(3-methyl-2,2-dioxido-2,1,3-benzothiadiazol-1(3H)-yl)propan-1-amine;
  N-methyl-3-(3-methyl-2,2-dioxido-2,1,3-benzo thiadiazol-1(3H)-yl)-3-phenylpropan-1-amine;
  N-methyl-3-(3-methyl-2,2-dioxido-2,1,3-benzothiadiazol-1(3H)-yl)-3-phenylpropan-1-amine;
  3-(3-isopropyl-2,2-dioxido-2,1,3-benzothiadiazol-1(3H)-yl)-N-methyl-3-phenylpropan-1-amine;
  3-(3-fluorophenyl)-3-(3-isopropyl-2,2-dioxido-2,1,3-benzothiadiazol-1(3H)-yl)-N-methylpropan-1-amine; or
  a pharmaceutically acceptable salt thereof.

Especially preferred compounds include:
  (3R)-3-[3-(4-chlorophenyl)-2,2-dioxido-2,1,3-benzothiadiazol-1(3H)-yl]-N-methyl-3-phenylpropan-1-amine;

(3R)-3-(3-chloro-5-fluorophenyl)-3-(3-isopropyl-2,2-dioxido-2,1,3-benzothiadiazol-1(3H)-yl)-N-methylpropan-1-amine hydrochloride;

(3R)-3-(3-chloro-5-fluorophenyl)-N-methyl-3-(3-methyl-2,2-dioxido-2,1,3-benzothiadiazol-1(3H)-yl)propan-1-amine hydrochloride;

(3R)-N-methyl-3-(3-methyl-2,2-dioxido-2,1,3-benzo thiadiazol-1(3H)-yl)-3-phenylpropan-1-amine hydrochloride;

(3S)-N-methyl-3-(3-methyl-2,2-dioxido-2,1,3-benzothiadiazol-1(3H)-yl)-3-phenylpropan-1-amine hydrochloride;

(3R)-3-(3-isopropyl-2,2-dioxido-2,1,3-benzothiadiazol-1(3H)-yl)-N-methyl-3-phenylpropan-1-amine;

(3R)-3-(3-fluorophenyl)-3-(3-isopropyl-2,2-dioxido-2,1,3-benzothiadiazol-1(3H)-yl)-N-methylpropan-1-amine hydrochloride; or a pharmaceutically acceptable salt thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, *J. of Pharmaceutical Sciences*, 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale. Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature.

The compounds of this invention contain chiral centers, providing various stereoisomeric forms such as enantiomeric mixtures as well as optical isomers. The individual optical isomers can be prepared directly through asymmetric and/or stereospecific synthesis or by conventional chiral separation of optical isomers from the enantiomeric mixture.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

In accordance with this invention, compounds of formula I are produced by the following reaction schemes (Schemes I to VI). In accordance with this invention, compounds of formula I are produced by the following reaction schemes (Schemes I to VI). Depending on the desired diastereomer, the compounds can be prepared via two different synthetic routes (A and B, Schemes I and II). If it is desired to synthesize compounds of formula I-a, they can be prepared from compounds of formula 4 by selectively converting the primary alcohol into a leaving group and displacing it with a desired amine. (Route A, Scheme I) Any conventional method for the selective conversion of a primary alcohol into a leaving group, and any conventional method for displacing a primary leaving group with an amine can be utilized for this conversion. In accordance with the preferred embodiment of this invention, the diol of formula 4 is treated with para-toluenesulfonyl chloride in pyridine to form the tosylate of formula 5, which is converted to the compound of formula I-a by treatment with an excess of alcoholic amine solution, either at room temperature or heated to about 40° C. to about 80° C. in a sealed tube. Compounds of formula I-a can be converted to a pharmaceutically acceptable salt using any conventional method.

embodiment of this invention, compounds of formula 6 are reacted with an alkyl halide using sodium hydride as base to form compounds of formula 8, which can be deprotected to form compounds of formula 9 via any conventional method for deprotection of a primary alcohol. According to the preferred embodiment of this invention, compounds of formula 8 are treated with dilute aqueous hydrochloric acid or trifluoroacetic acid in dichloromethane to form compounds of formula 9. Conversion of the primary alcohol in compounds of formula 9 to complete the synthesis of compounds of formula I-aa can be performed as previously described for the synthesis of compounds of formula I-a. Compounds of formula I-aa can be converted to a pharmaceutically acceptable salt using any conventional method.

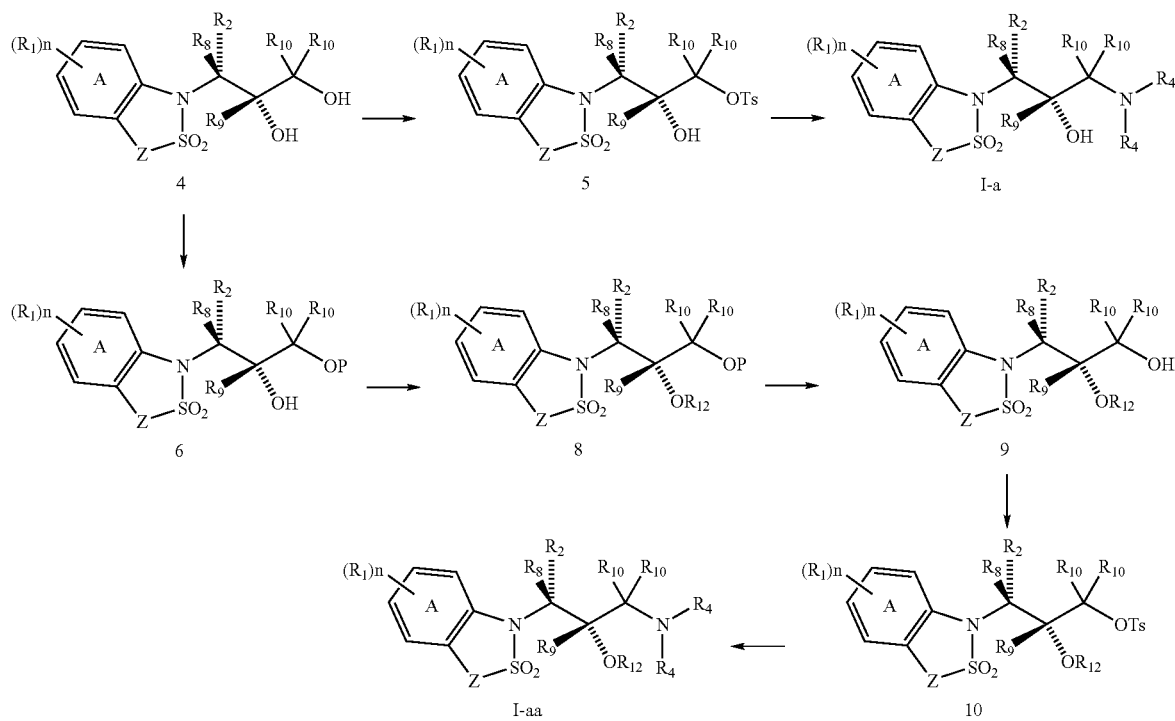

Scheme I wherein: A, Z, $R_1$, n, $R_2$, $R_4$, $R_8$, $R_9$, $R_{10}$, $R_{12}$ are as previously described.

P=protecting group; preferably trimethylsilyl, tert-butyldimethylsilyl, para-nitrobenzoyl; and OTs=para-toluenesulfonylate or any conventional leaving group If it is desired to form compounds of formula I-aa, they can be prepared from compounds of formula 4 via selective protection of the primary alcohol, followed by alkylation of the secondary alcohol, and deprotection of the primary alcohol. Any conventional alcohol protecting groups can be utilized for this conversion and any method for the selective protection of a primary alcohol can be employed. According to the preferred embodiment of this invention, the reaction is carried out at low temperature in dichloromethane with trimethylsilyl chloride and triethylamine as base to form compounds of formula 6. Alkylation of the secondary alcohol can be accomplished via any conventional method of alkylating a secondary alcohol found in the literature. According to the preferred Alternatively, compounds of formula 10 can be prepared directly from compounds of formula 5. Any method of alkylating a hydroxyl group in the presence of a tosyl group can be employed for this conversion. In accordance with the preferred embodiment of this invention, compounds of formula 5 are treated with an alkyl trifluoromethanesulfonate, e.g. methyl trifluoromethanesulfonate, in the presence of a hindered base, e.g. 2,6-di-tert-butyl-4-methylpyridine. The reaction can be performed either at room temperature or heated to about 40° C. to about 80° C. Compounds of formula 10 can be converted to compounds of formula I-aa as previously described for the synthesis of compounds of formula I-a. Compounds of formula I-aa can be converted to a pharmaceutically acceptable salt using any conventional method.

If it is desired to form compounds of formula I-b, they can also be prepared from compounds of formula 4 via Route B (Scheme II). This route involves the selective protection of the primary alcohol followed by conversion of the secondary alcohol to a leaving group. Any conventional method for the selective protection of a primary alcohol, and any conventional method for converting of a secondary alcohol into a leaving group can be utilized for this conversion. In accordance with the preferred embodiment of this invention, compounds of formula 4 are treated with para-nitrobenzoyl chloride in pyridine at low temperature (preferably below about 0° C.) to form compounds of formula 11. Compounds of formula 11 can be converted to a secondary mesylate of formula 12 via reaction with methanesulfonyl chloride in dichloromethane using triethylamine as base. The reaction is preferably carried out at temperatures between about −15° C. and about 10° C. Deprotection of the primary alcohol in compounds of formula 12 allows for the formation of a primary epoxide through an $S_N2$ reaction resulting in an inversion of the stereocenter at C2. Any conventional method for deprotection of a primary alcohol, and any conventional method for epoxide formation onto an alpha leaving group can be employed for this conversion. In accordance with the preferred embodiment of this invention, compounds of formula 12 are treated with an aqueous solution of a suitable base in organic solvent, preferably, aqueous sodium hydroxide in dioxane. The resulting epoxide of formula 13 can be ring-opened regioselectively with a suitable amine to produce the desired aminoalcohol of formula I-b. Any conventional method for the regioselective ring opening of a primary epoxide can be employed for this conversion. In accordance with the preferred embodiment of this invention, compounds of formula 13 are treated with an excess of an alcoholic amine solution in a sealed flask, either at room temperature or heated to about 40° C. to about 90° C. Compounds of formula I-b can be converted into a pharmaceutically acceptable salt using conventional methods.

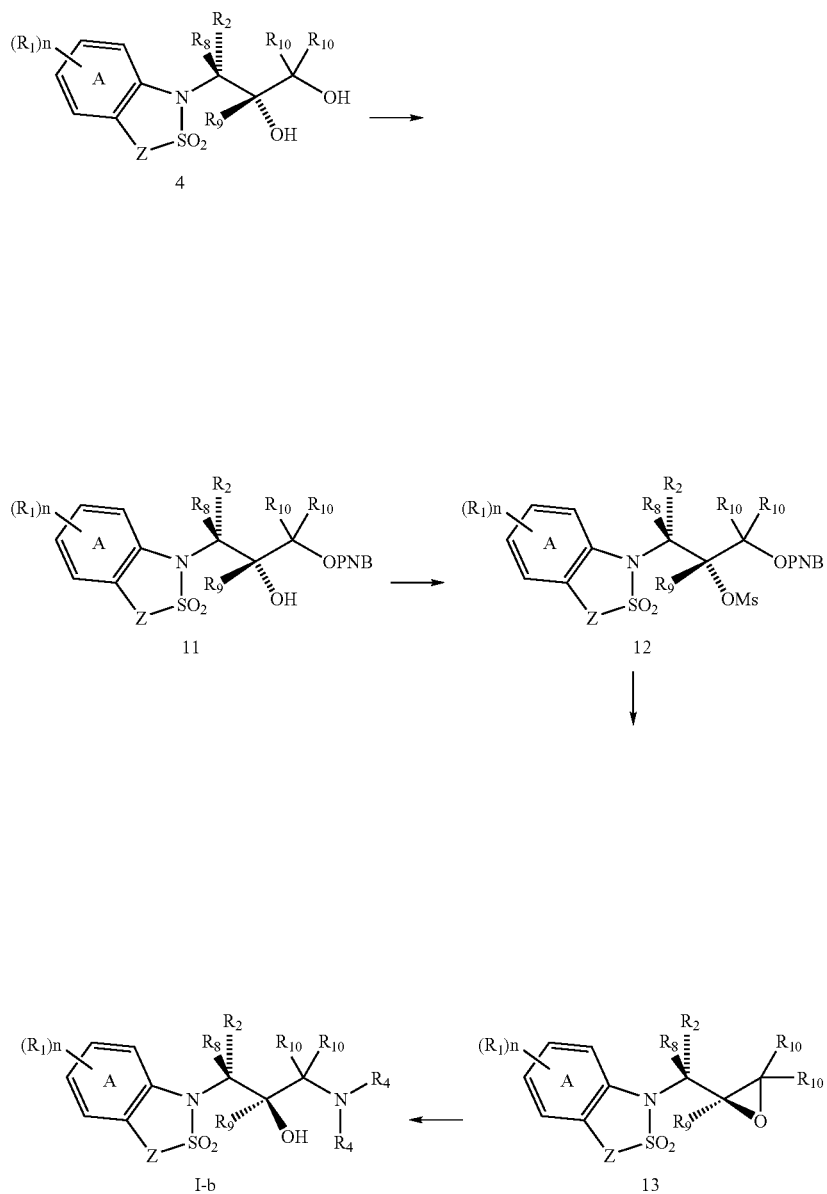

Scheme II wherein: A, Z, $R_1$, n, $R_2$, and $R_4$, $R_8$, $R_{10}$ are as previously described $R_9$ is H PNB=para-nitrobenzoyl or any conventional protecting group; and OMs=methanesulfonate or any conventional leaving group If it is desired to form compounds of formula I-bb, they can be made from compounds of formula I-b via protection of the amine, alkylation of the secondary alcohol and deprotection of the amine (Scheme III). Any conventional method for protection of an amine, alkylation of a secondary alcohol, and deprotection of an amine can be utilized for this conversion. In accordance with the preferred embodiment of this invention, compounds of formula I-b are treated with boc anhydride, where boc=tert-butoxycarbonyl, to form compounds of formula 14 which can be alkylated with an alkyl halide using sodium hydride as base to form compounds of formula 15. Deprotection is accomplished using an acid, preferably trifluoroacetic acid in dichloromethane to form compounds of formula I-bb that can be converted into a pharmaceutically acceptable salt using conventional methods.

wherein: A, Z, $R_1$, n, $R_2$, and $R_4$, $R_8$, $R_9$, $R_{10}$ are as previously described $R_{12}$=$C_1$-$C_3$ lower alkyl, P=protecting group, preferably tert-butoxycarbonyl

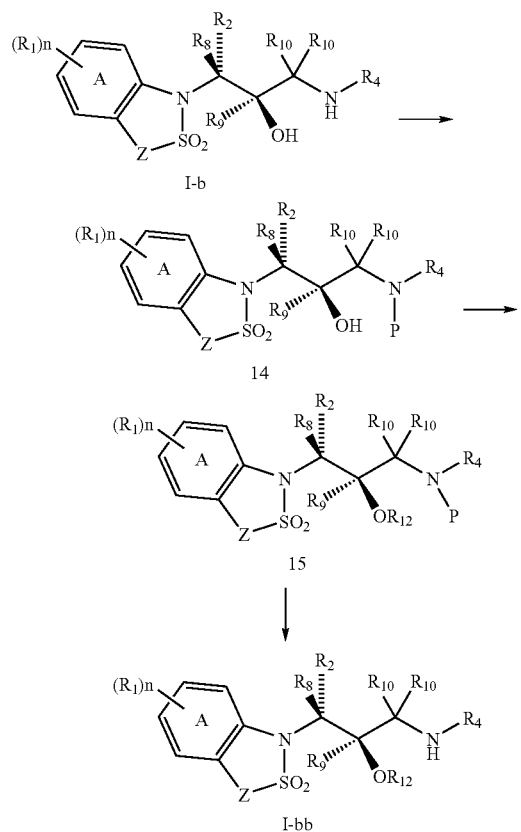

Compounds of formula I-a (when $R_3$ is other than $OR_{12}$) can be prepared from compounds of formula 16 by displacing a terminal leaving group with a desired amine (Scheme IV). Any conventional method for displacing a primary leaving group with an amine can be utilized for this conversion. In accordance with the preferred embodiment of this invention, the alkyl chloride of formula 16 is treated with a suitable amine in the presence of a nucleophilic iodide reagent such as potassium iodide or sodium iodide in an alcoholic solvent, e.g., methanol or ethanol to furnish compounds of formula I-a (when $R_3$ is other than $OR_{12}$). The reaction is generally executed in a sealed tube at the elevated temperature ranging from 40 to 90° C. Compounds of formula I-a (when $R_3$ is other than $OR_{12}$) can be converted into a pharmaceutically acceptable salt using conventional methods.

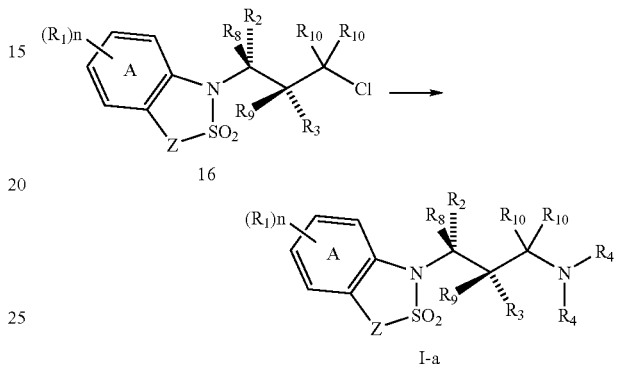

Compounds of formula 4 may be formed via a regio- and stereo-selective ring opening of an appropriately substituted epoxide of formula 18 (formed via an epoxidation of an appropriately substituted allylic alcohol) with an appropriately substituted compound of formula 17 (Scheme V). Any conventional method for the regio- and stereo-selective ring opening of an epoxide can be employed for this conversion. In accordance with the preferred embodiment of this invention, compounds of formula 17 are treated with a base, e.g. sodium hydroxide, sodium hydride, sodium tert-butoxide, potassium hydroxide, potassium tert-butoxide, then treated with the epoxide of formula 18 in a suitable solvent including but not limited to THF, DMF, water, methylene chloride, and ethanol. The epoxide of formula 18 can be pre-treated with a Lewis acid, e.g. titanium iso-propoxide, boron-trifluoride, etc. to enhance regio-selective ring opening. The reaction can be effected at the temperature ranging from room temperature to 80° C. over a duration of about 2 hours to about 72 hours. Alternatively, compounds of formula 17 that are suitably nucleophilic, e.g. indoline, can be heated with the epoxide of formula 18 at temperatures from about 50° C. to about 170° C. to form compounds of formula 4.

Epoxidation of trans-allylic alcohols can be performed either racemically or asymmetrically using methods described in the literature. In accordance with the preferred embodiment of this invention, racemic epoxidation is conducted with either peracetic acid or meta-chloroperbenzoic acid. If it is desired to produce a single enantiomer of compounds of formula I, asymmetric epoxidation of an allylic alcohol can be performed with tert-butylhydroperoxide or cumene hydroperoxide in the presence of the appropriate tartrate ester, titanium (IV) isopropoxide, and molecular sieves. This method is well established in the literature (e.g. K. B. Sharpless, et. al., *J. Org. Chem.* 1986, 51, 3710). Compounds of formula 17 and the starting allylic alcohols are either available from commercial sources or are accessible through methods well established in the literature.

Scheme V

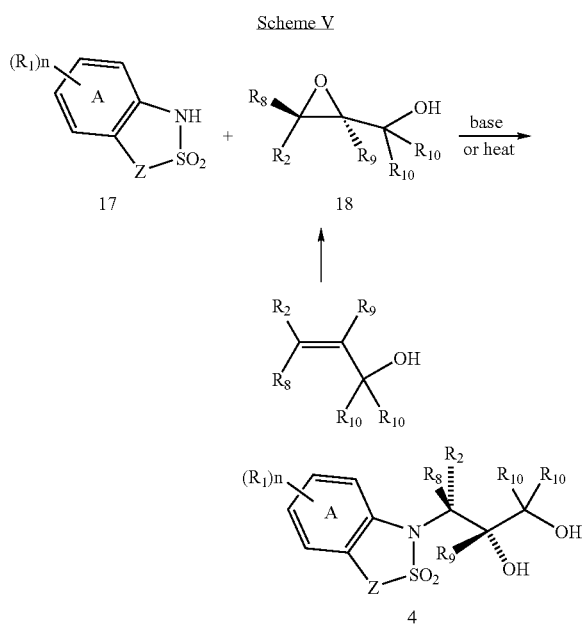

wherein: A, Y, Z, $R_1$, n, $R_8$, $R_9$, $R_{10}$ and $R_2$ are as previously described.

Compounds of formula 16 may be prepared as illustrated in Scheme VI. The hydroxyl group of compounds of formula 19 can be activated and subsequently replaced by an anion generated from compounds of formula 17 to produce compounds of formula 16. Any conventional method for activating a hydroxyl group of compounds of formula 19 and any conventional method for generating an anion of compounds of formula of 17 and subsequently replacing the activated hydroxyl group can be utilized for this conversion. In accordance with the preferred embodiment of this invention, the hydroxyl group of an appropriately substituted 3-chloropropanol of formula 19 can be activated via a Mitsunobu protocol and treated with compounds of formula 17 to produce compounds of formula 16. The Mitsunobo procedure is well documented (e.g., Hughes, David L., *Organic Preparations and Procedures International* (1996), 28(2), 127-64.). In accordance with the preferred embodiment of this invention, compounds of formula 16 may be effected by treatment of a mixture of compound 17, 19, and triphenylphosphine in an aprotic solvent such as THF with DIAD (diisopropyl azodicarboxylate). The reaction is generally executed at the room temperature under a blanket of inert gas with an approximate duration of 2 to 72 hours.

Scheme VI

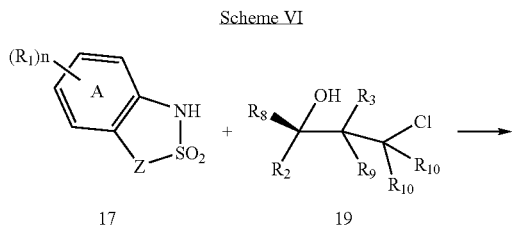

-continued

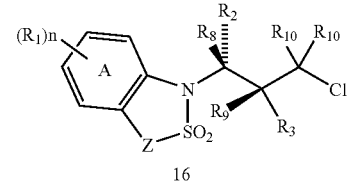

In other embodiments, the invention is directed to pharmaceutical compositions, comprising:
a. at least compound of formula I, or pharmaceutically acceptable salt thereof; and
b. at least one pharmaceutically acceptable carrier.

Generally, the compound of formula I, or a pharmaceutically acceptable salt thereof, will be present at a level of. from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I, or pharmaceutically acceptable salt thereof, with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromylagia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, noncardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain, cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

As used herein, "pain," includes both acute pain and chronic pain, which may be centralized pain, peripheral pain, or combination thereof. The term includes many different types of pains including, but not limited to, neuropathic pain, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purpose of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

In one embodiment, the present invention is directed to methods for treating or preventing vasomotor symptoms in a subject in need thereof, comprising the step of:

administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
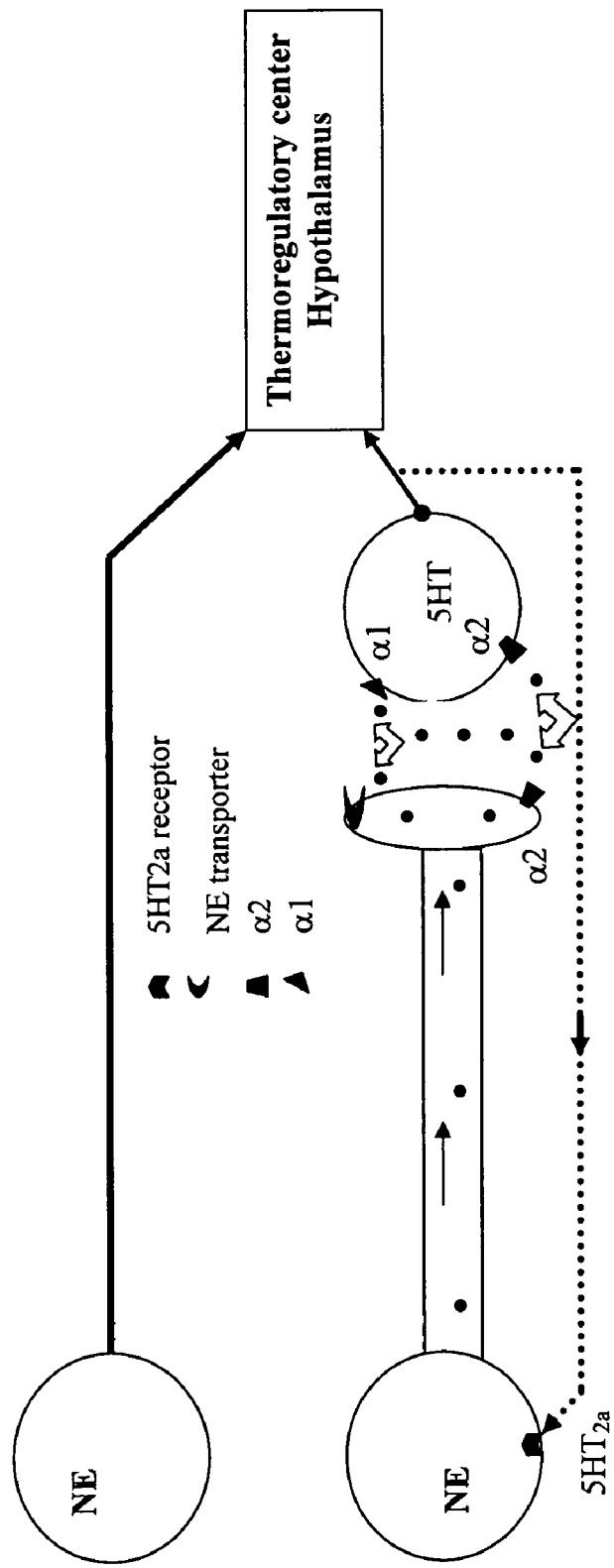
FIG. 2 is a schematic representation of the interactions of norepinephrine and serotonin and their respective receptors (5-$HT_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha1}$ and adrenergic$_{\alpha2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:
administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:
administering to said subject an effective amount of a compound of formula I or pharmaceutically acceptable salt thereof.

In another embodiment, the present invention is directed to methods for treating or preventing fibromylagia syndrome in a subject in need thereof, comprising the step of:
administering to said subject an effective amount of a compound of formula I or pharmaceutically acceptable salt thereof.

In further embodiments, the present invention is directed to methods for treating or preventing pain in a subject in need thereof, comprising the step of:
administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromylagia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

(3R)-3-[3-(4-chlorophenyl)-2,2-dioxido-2,1,3-benzothiadiazol-1(3H)-yl]-N-methyl-3-phenylpropan-1-amine

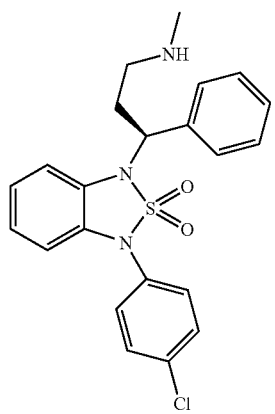

1-(4-chlorophenyl)-1,3-dihydro-2,1,3-benzothiadiazole 2,2-dioxide

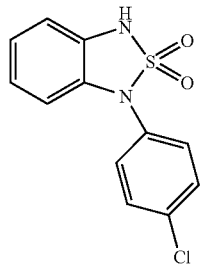

Dry diglyme (10 mL) was added to a flask under a nitrogen atmosphere and brought to a vigorous reflux (oil bath maintained at 190° C.). A solution of N-(4-chloro-phenyl)-benzene-1,2-diamine (1.09 g, 5.0 mmol) and sulfamide (0.58 g, 6 mmol) in diglyme (5 mL) was added dropwise to the refluxing solution over 15 minutes. The mixture was refluxed an additional 15 minutes and then cooled and diluted with ether, washed with 2N HCl, water, and saturated brine. The organic layer was separated, dried over anhydrous magnesium sulfate, filtered, and concentrated in vacuo. The crude product was dissolved in ether and passed though a plug of silica gel to give 1-(3-bromopropyl)-3-(4-chlorophenyl)-1,3-dihydro-2,1,3-benzothiadiazole 2,2-dioxide (0.66 g, 47%).

MS (ESI) m/z 279;

HPLC purity 94.7% at 210-370 nm, 9.3 min.; Xterra RP18, 3.5 u, 150×4.6 mm column, 1.2 mL/min, 85/15-5/95 (Ammon. Form. Buff. Ph=3.5/ACN+MeOH) for 10 minutes, hold 4 minutes.

1-(4-Chloro-phenyl)-3-(3-chloro-1-phenyl-propyl)-1,3-dihydro-benzo[1,2,5]-thiadiazole 2,2-dioxide

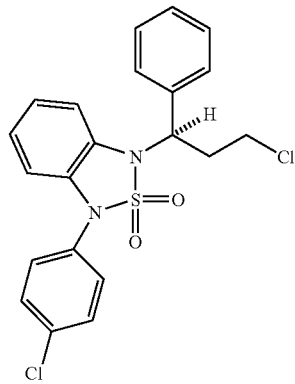

To a mixture of 1-(3-bromopropyl)-3-(4-chlorophenyl)-1,3-dihydro-2,1,3-benzothiadiazole 2,2-dioxide (0.28 g, 1.0 mmol), (S)-(−)-3-chloro-1-phenyl-1-propanol (0.17 g, 1.0 mmol), and triphenylphosphine (314 mg, 1.2 mmol) in anhydrous THF (15 mL) was added DIAD (0.23 mL, 1.2 mmol) under nitrogen at 25° C. The mixture was stirred for 16 hours followed by concentration of the mixture in vacuo. The crude product was purified via Isco chromatography (Redisep, silica, gradient 5-40% ethyl acetate in hexane) to afford 0.17 g of 1-(4-Chloro-phenyl)-3-(3-chloro-1-phenyl-propyl)-1,3-dihydro-benzo[1,2,5]-thiadiazole 2,2-dioxide that was immediately carried on to the next step. MS (ESI) m/z [M−H]⁻ 431;

(3R)-3-[3-(4-chlorophenyl)-2,2-dioxido-2,1,3-benzothiadiazol-1(3H)-yl]-N-methyl-3-phenylpropan-1-amine

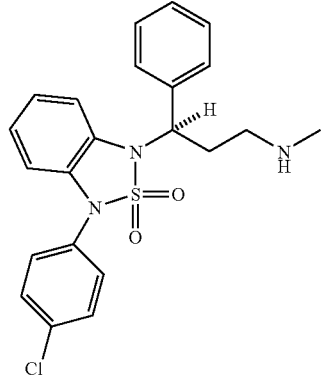

1-(4-Chloro-phenyl)-3-(3-chloro-1-phenyl-propyl)-1,3-dihydro-benzo[1,2,5]-thiadiazole 2,2-dioxide (0.12 g) was dissolved in methylamine (8M in ethanol, 20 mL), sodium iodide (58 mg, 0.39 mmol) was added and the mixture stirred for 96 hours. The mixture was concentrated in vacuo and purified via chromatography (silica, 5% methanol saturated with ammonia in chloroform) to give (3R)-3-[3-(4-chlorophenyl)-2,2-dioxido-2,1,3-benzothiadiazol-1(3H)-yl]-N-methyl-3-phenylpropan-1-amine as a colorless oil. The free-base was dissolved in methanol (5 mL) and treated with 2N aqueous hydrochloric acid (1.0 equivalent) and concentrated. The residue was dissolved in water and lyophilized to give 130 mg (72%) (3R)-3-[3-(4-chlorophenyl)-2,2-dioxido-2,1,3-benzothiadiazol-1(3H)-yl]-N-methyl-3-phenylpropan-1-amine as hydrochloride salt as a white powder. MS (ES) m/z 427.8.

Example 2

(3R)-3-(3-chloro-5-fluorophenyl)-3-(3-isopropyl-2,2-dioxido-2,1,3-benzothiadiazol-1(3H)-yl)-N-methylpropan-1-amine hydrochloride

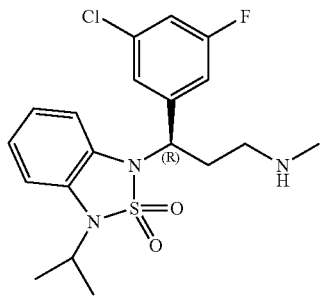

Step 1: A reaction flask (500 mL) containing zinc chloride (6.98 g, 51.2 mmol) was dried by heating using a heat gun under vacuum. After cooling to room temperature, a solution of 3-chloro-5-fluorophenylmagnesium bromide (0.5 M in dry tetrahydrofuran, 100 mL, 50.0 mmol) was added to the reaction flask via a cannula, and the mixture was stirred until all zinc chloride solid was dissolved and the formation of a sluggish bright yellow solution (~1 h). A warm bath (40° C) may be applied to complete this process. Anhydrous tetrahydrofuran (100 mL) was added, followed by tetrakis(triphenylphosphine)palladium (2.89 g, 2.50 mmol, 0.05 equiv.). After cooling to 0° C., 3-chloropropionyl chloride (5.05 mL, 52.5 mmol, 1.05 equiv.) was added dropwise and the mixture was stirred at 0° C. for 2 hours. The reaction mixture was acidified with an aqueous hydrochloric acid solution (3 N), then extracted with diethyl ether (2×250 mL). The combined ether extracts were washed with a saturated aqueous sodium bicarbonate solution, brine, dried (anhydrous sodium sulfate), and concentrated. The crude oil was purified by Isco CombiFlash Companion column chromatography (silica gel, 0-15% ethyl acetate/hexane) and the resulting white solid was recrystallized (minimal diethyl ether/hexane/−25° C.) to give pure 3-chloro-1-(3-chloro-5-fluorophenyl)propan-1-one as a white powder (5.54 g, 50%).

Step 2: To a mixture of (R)-2-methyl-CBS-oxazaborolidine (1.0 M in toluene, 1.5 mL, 1.5 mmol, 0.1 equiv.) in tetrahydrofuran (10 mL) under a nitrogen atmosphere at −25° C. was added a solution of borane (1.0 M in tetrahydrofuran, 9.0 mL, 9.0 mmol, 0.6 equiv.). A solution of 3-chloro-1-(3-chloro-5-fluorophenyl)propan-1-one (3.32 g, 15.0 mmol) in tetrahydrofuran (10 mL) was added dropwise over a period of 25 min, and the reaction mixture was stirred for an additional 30 min at −25° C. Methanol (10 mL) was added slowly to quench the reaction, followed by the slow addition of hydrogen chloride solution (1.0 M in diethyl ether, 20 mL) at −25° C. All volatiles were removed under reduced pressure. Hexane (100 mL) was added, and the white salt of the chiral auxiliary was filtered through a pad of celite and washed with hexane (2×25 mL). The filtrate was concentrated under reduced pressure to give (1S)-3-chloro-1-(3-chloro-5-fluorophenyl)propan-1-ol as viscous, colorless oil (Yield: 3.34 g (100%). Chiral purity: 93.4%, $[\alpha]_D^{25}=-10.3°$ (c=10 mg/mL, $CHCl_3$)). This material was dissolved in 70 mL of methanol/acetonitrile. 500 μL of the resulting solution was repetitively injected onto the Supercritical Fluid Chromatography instrument, and the baseline resolved enantiomers were separately collected using the conditions described below. The chiral purity of each enantiomer was determined under the same Supercritical Fluid Chromatography conditions using a Chiralpak AD-H 5μm, 250 mm×4.6 mm ID column at 2.0 mL/min flow rate using Analytical Supercritical Fluid Chromatography (Berger Instruments, Inc. Newark, Del.). The chiral purity of the product was found to be 99.8%.

SFC Instrument: Berger MultiGram Prep SFC (Berger Instruments, Inc. Newark, Del.)

| Column: | Chiralpak AD-H; 5μm; 250 mm L × 20 mm ID (Chiral Technologies, Inc, Exton, PA) |
|---|---|
| Column temperature: | 35° C. |
| SFC Modifier: | 20% MeOH/80% $CO_2$ |
| Flow rate: | 50 mL/min |
| Outlet Pressure: | 100 bar |
| Detector: | UV at 220 nm |

Step 3: To a solution of 1-fluoro-2-nitrobenzene (14.11 g, 100 mmol) in ethanol (50 mL) was added isopropylamine (30 mL, 350 mmol, 3.5 equiv.) and the mixture was heated at 55° C. with stirring in a sealed reaction vessel for 3 hours. All volatiles were removed under reduced pressure. The residue was dissolved in diethyl ether (300 mL) and the solution was washed with a saturated aqueous sodium bicarbonate solution, brine, dried (anhydrous sodium sulfate), and concentrated to give N-isopropyl-2-nitroaniline as a bright orange liquid. This was in ethanol (50 mL) and Raney nickel (2.8 g) was added. The mixture was stirred under a hydrogen atmosphere (30 psi) until all starting material was consumed (as evidenced by the disappearance of the bright orange color, ~3 h). The reaction mixture was filtered through a pad of celite and concentrated to give 14.92 g (98%) N-isopropyl-1,2-phenylenediamine as a viscous black liquid.

Step 4: To a solution of N-isopropyl-1,2-phenylenediamine (7.52 g, 50.0 mmol) in pyridine (200 mL) was added sulfamide (7.21 g, 75 mmol, 1.5 equiv.) and the mixture was refluxed for 1 hour. After cooling, pyridine was removed under reduced pressure. Residual pyridine was removed by azeotrope evaporation using toluene. The black residue was dissolved in chloroform (150 mL) and the solution was washed with an aqueous hydrochloric acid solution (2 N, 2×50 mL), water, brine, dried (anhydrous sodium sulfate), and concentrated to give a crude black oil, which was purified by Isco CombiFlash Companion column chromatography (silica gel, 0-40% ethyl acetate/hexane, with 1% formic acid additive) to give 8.61 g (81%) of 1-isopropyl-1,3-dihydro-2,1,3-benzothiadiazole 2,2-dioxide as a viscous brown liquid. MS (ES) m/z 211 ([M−H]$^-$).

Step 5: To mixture of 1-isopropyl-1,3-dihydro-2,1,3-benzothiadiazole 2,2-dioxide (1.28 g, 6.00 mmol), (1S)-3-chloro-1-(3-chloro-5-fluorophenyl)propan-1-ol (1.34 g, 6.00 mmol) and triphenylphosphine (1.73 g, 6.60 mmol, 1.1 equiv.) in tetrahydrofuran (20 mL) under nitrogen was added slowly diisopropyl azodicarboxylate (1.28 mL, 6.60 mmol, 1.1 equiv.) via a syringe at 0° C. The resulting solution was stirred at room temperature overnight. Solvent was removed under reduced pressure and the viscous brown liquid residue was purified using Isco CombiFlash Companion column chromatography (silica gel, 0-15% ethyl acetate/hexane) to give 2.06 g (82%) of 1-[(1R)-3-chloro-1-(3-chloro-5-fluorophenyl)propyl]-3-isopropyl-1,3-dihydro-2,1,3-benzothiadiazole 2,2-dioxide as a white solid.

Step 6: 1-[(1R)-3-chloro-1-(3-chloro-5-fluorophenyl)propyl]-3-isopropyl-1,3-dihydro-2,1,3-benzothiadiazole 2,2-dioxide (1.75 g, 4.19 mmol) and ethanolic solution of methylamine (33% in ethanol, 30 mL) was heated at 85° C for 4 hours with stirring in a sealed reaction vessel. Upon cooling, all volatiles were removed under reduced pressure. The resulting residue was dissolved in dichloromethane (50 mL), washed with aqueous potassium carbonate (20 mL), dried (anhydrous sodium sulfate), and concentrated. Purification by Isco CombiFlash Companion column chromatography (silica gel, 0-15% methanol/dichloromethane, with 0.5% triethylamine additive) gave 1.22 g (70%) of (3R)-3-(3-chloro-5-fluorophenyl)-3-(3-isopropyl-2,2-dioxido-2,1,3-benzothiadiazol-1(3H)-yl)-N-methylpropan-1-amine as a white foam, which was dissolved in dichloromethane (20 mL) and treated with an ethereal solution of hydrochloric acid (1 M, 3.3 mL, 3.3 mmol). To the resulting solution was added hexane until white powder formed, which was collected, washed with hexane, and dried in vacuo to yield (3R)-3-(3-chloro-5-fluorophenyl)-3-(3-isopropyl-2,2-dioxido-2,1,3-benzothiadiazol-1(3H)-yl)-N-methylpropan-1-amine hydrochloride as a white powder. MS (ES) m/z 411.9 ([M+H]$^{30}$); HRMS: calculated for $C_{19}H_{23}ClFN_3O_2S+H^+$, 412.1256; found (ESI, [M+H]$^{30}$), 412.1266.

Example 3

(3R)-3-(3-chloro-5-fluorophenyl)-N-methyl-3-(3-methyl-2,2-dioxido-2,1,3-benzothiadiazol-1(3H)-yl)propan-1-amine hydrochloride

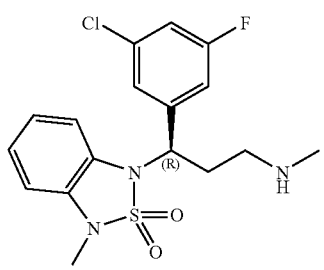

In an analogous manner to Example 2, step 4, 1-methyl-1,3-dihydro-2,1,3-benzothiadiazole 2,2-dioxide was prepared from N-methyl-1,2-phenylenediamine as a white solid. MS (ES) m/z 183.1 ([M–H]$^-$).

In an analogous manner to Example 2, step 5, 1-[(1R)-3-chloro-1-(3-chloro-5-fluorophenyl)propyl]-3-methyl-1,3-dihydro-2,1,3-benzothiadiazole 2,2-dioxide was prepared from 1-methyl-1,3-dihydro-2,1,3-benzothiadiazole 2,2-dioxide and (1S)-3-chloro-1-(3-chloro-5-fluorophenyl)propan-1-ol (Example 2, step 2) as a viscous, colorless liquid.

In an analogous manner to Example 2, step 6, (3R)-3-(3-chloro-5-fluorophenyl)-N-methyl-3-(3-methyl-2,2-dioxido-2,1,3-benzothiadiazol-1(3H)-yl)propan-1-amine hydrochloride was prepared from 1-[(1R)-3-chloro-1-(3-chloro-5-fluorophenyl)propyl]-3-methyl-1,3-dihydro-2,1,3-benzothiadiazole 2,2-dioxide as a white powder. MS (ES) m/z 383.8 ([M+H]$^+$); HRMS: calculated for $C_{17}H_{19}ClFN_3O_2S+H^+$, 384.0943; found (ESI, [M+H]$^{30}$), 384.0951.

Example 4

(3R)-N-methyl-3-(3-methyl-2,2-dioxido-2,1,3-benzothiadiazol-1(3H)-yl)-3-phenylpropan-1-amine hydrochloride

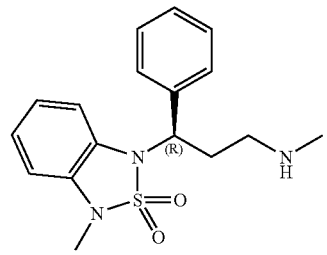

In an analogous manner to Example 2, step 5, 1-[(1R)-3-chloro-1-phenylpropyl]-3-methyl-1,3-dihydro-2,1,3-benzothiadiazole 2,2-dioxide was prepared from 1-methyl-1,3-dihydro-2,1,3-benzothiadiazole 2,2-dioxide (Example 5, step 1) and (S)-(−)-3-chloro-1-phenyl-1-propanol as a white solid.

In an analogous manner to Example 2, step 6, (3R)-N-methyl-3-(3-methyl-2,2-dioxido-2,1,3-benzothiadiazol-1(3H)-yl)-3-phenylpropan-1-amine hydrochloride was prepared from 1-[(1R)-3-chloro-1-phenylpropyl]-3-methyl-1,3-dihydro-2,1,3-benzothiadiazole 2,2-dioxide a white powder. MS (ES) m/z 331.9 ([M+H]$^+$); HRMS: calculated for $C_{17}H_{21}N_3O_2S+H^+$, 332.1427; found (ESI, [M+H]$^+$), 332.1423.

Example 5

(3S)-N-methyl-3-(3-methyl-2,2-dioxido-2,1,3-benzothiadiazol-1(3H)-yl)-3-phenylpropan-1-amine hydrochloride

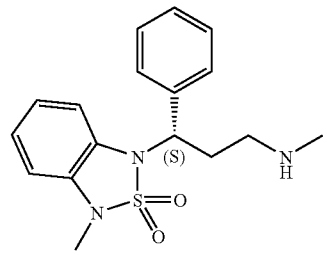

In an analogous manner to Example 2, step 5, 1-[(1S)-3-chloro-1-phenylpropyl]-3-methyl-1,3-dihydro-2,1,3-benzothiadiazole 2,2-dioxide was prepared from 1-methyl-1,3-dihydro-2,1,3-benzothiadiazole 2,2-dioxide (Example 5, step 1) and (R)-(+)-3-chloro-1-phenyl-1-propanol as a white solid. MS (ES) m/z 336.8 ([M+H]$^+$).

In an analogous manner to Example 2, step 6, (3S)-N-methyl-3-(3-methyl-2,2-dioxido-2,1,3-benzothiadiazol-1(3H)-yl)-3-phenylpropan-1-amine hydrochloride was prepared from 1-[(1S)-3-chloro-1-phenylpropyl]-3-methyl-1,3-dihydro-2,1,3-benzothiadiazole 2,2-dioxide as a white

Example 6

(3R)-3-(3-isopropyl-2,2-dioxido-2,1,3-benzothiadiazol-1(3H)-yl)-N-methyl-3-phenylpropan-1-amine

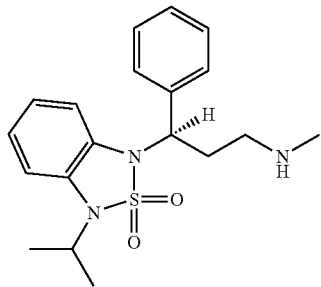

In an analogous manner to Example 2, step 5, 1-[(1R)-3-chloro-1-phenylpropyl]-3-isopropyl-1,3-dihydro-2,1,3-benzothiadiazole 2,2-dioxide was prepared from 1-isopropyl-1,3-dihydro-2,1,3-benzothiadiazole 2,2-dioxide and (S)-(−)-3-chloro-1-phenyl-1-propanol. MS (ES) m/z 364.9.

In an analogous manner to Example 2, step 6, 1-isopropyl-1,3-dihydro-2,1,3-benzothiadiazole 2,2-dioxide (3R)-3-(3-isopropyl-2,2-dioxido-2,1,3-benzothiadiazol-1(3H)-yl)-N-methyl-3-phenylpropan-1-amine hydrochloride was prepared from 1-[(1R)-3-chloro-1-phenylpropyl]-3-isopropyl-1,3-dihydro-2,1,3-benzothiadiazole 2,2-dioxide and methyl amine. MS (ES) m/z 360.1; HRMS: calculated for $C_{19}H_{25}N_3O_2S+H^+$, 360.17402; found (ESI, [M+H]$^+$), 360.1754; $[\alpha]_D^{25}$=57.4° (c=10 mg/mL, MeOH).

Example 7

(3R)-3-(3-fluorophenyl)-3-(3-isopropyl-2,2-dioxido-2,1,3-benzothiadiazol-1(3H)-yl)-N-methylpropan-1-amine hydrochloride

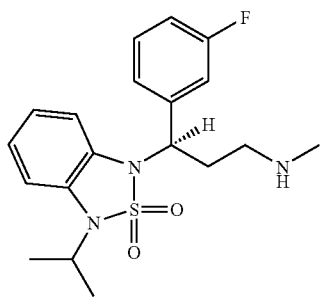

In an analogous manner to Example 2, steps 1 and 2, (1S)-3-chloro-1-(3-fluorophenyl)propan-1-ol was prepared from 3-fluorophenylmagnesium bromide and 3-chloropropionyl chloride as a colorless oil. MS (ES) m/z 187.2; $[\alpha]_D^{25}$=−15.2° (c=10 mg/mL, CHCl$_3$).

In an analogous manner to Example 2, step 5 1-[(1R)-3-chloro-1-(3-fluorophenyl)propyl]-3-isopropyl-1,3-dihydro-2,1,3-benzothiadiazole 2,2-dioxide was prepared from 1-isopropyl-1,3-dihydro-2,1,3-benzothiadiazole 2,2-dioxide and (1S)-3-chloro-1-(3-fluorophenyl)propan-1-ol. MS m/z 382.1

In an analogous manner to Example 2, step 6 (3R)-3-(3-fluorophenyl)-3-(3-isopropyl-2,2-dioxido-2,1,3-benzothiadiazol-1(3H)-yl)-N-methylpropan-1-amine hydrochloride was prepared from 1-[(1R)-3-chloro-1-(3-fluorophenyl)propyl]-3-isopropyl-1,3-dihydro-2,1,3-benzothiadiazole 2,2-dioxide and methylamine. MS (ES) m/z 377.9; HRMS: calculated for $C_{19}H_{24}FN_3O_2S+H^+$, 378.16460; found (ESI, [M+H]$^+$), 378.1682.

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 □g/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498)

Norepinephrine (NE) Uptake Assay

On day 1, cells were plated at 3,000 cells/well in growth medium and maintained in a cell incubator (37° C., 5% CO$_2$). On day 2, growth medium was replaced with 200 µl of assay buffer (25 mM HEPES; 120 mM NaCl; 5 mM KCl; 2.5 mM CaCl$_2$; 1.2 mM MgSO$_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 µl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C.). The reaction was terminated by decanting the supernatant from the plate. The plates containing cells were washed twice with 200 µl assay buffer (37° C.) to remove free radioligand. The plates were then inverted, left to dry for 2 minutes, then reinverted and air-dried for an additional 10 minutes. The cells were lysed in 25 µl of 0.25 N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 μl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 μM pargyline. A stock solution of paroxetine (AHR-4389-1) was prepared in DMSO (10 mM) and delivered to triplicate wells containing cells for a final test concentration of 1 μM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 μl of assay buffer. The cells were incubated with the compound for 10 minutes (37° C.). To initiate the reaction, [$^3$H]hydroxytryptamine creatinine sulfate diluted in assay buffer was delivered in 25 μl aliquots to each well for a final test concentration of 15 nM. The cells were incubated with the reaction mixture for 5 minutes at 37° C. The 5-HT uptake reaction was terminated by decanting the assay buffer. The cells were washed twice with 200 μl assay buffer (37° C.) to remove free radioligand. The plates were inverted and left to dry for 2 minutes, then reinverted and air-dried for an additional 10 minutes. Subsequently, the cells were lysed in 25 μl of 0.25 N NaOH (4° C.) then placed on a shaker table and shaken vigorously for 5 minutes. After cell lysis, 75 μl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 μM desipramine (hNET) or 1 μM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment.

The compounds of Examples 1 to 4 and 6 to 7 had an $IC_{50}$ (NET) ranging between about 50 nM to less than about 10 μM. Example 5 had 33% inhibition at hNET at 6 μM.

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

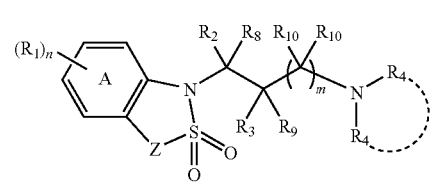

or a pharmaceutically acceptable salt thereof;

wherein:

Z is $NR_7$;

$R_1$ is, independently at each occurrence, alkyl, alkoxy, halo, $CF_3$, $OCF_3$, arylalkoxy substituted with 0 to 3 $R_{11}$, aryloxy substituted with 0 to 3 $R_{11}$, aryl substituted with 0 to 3 $R_{11}$, heteroaryl substituted with 0 to 3 $R_{11}$, hydroxy, alkanoytoxy, nitro, cyano, alkenyl, alkynyl, alkylsulfoxide, arylsulfoxide substituted with 0 to 3 $R_{11}$, alkylsulfone, arylsulfone substituted with 0 to 3 $R_{11}$, alkylsulfonamide, arylsulfonamide substituted with 0 to 3 $R_{11}$, heteroaryloxy substituted with 0 to 3 $R_{11}$, heteroarylmethoxy substituted with 0-3 $R_{11}$, alkylamido, or arylamido substituted with 0 to 3 $R_{11}$; or two adjacent $R_1$ represent methylenedioxy;

$R_2$ is aryl substituted with 0 to 3 $R_1$, or heteroaryl substituted with 0 to 3 $R_1$;

$R_3$ is H, F, $C_1$ to $C_4$ alkyl, or $OR_{12}$;

$R_{12}$ is H or $C_1$ to $C_4$ alkyl;

$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl, or both $R_4$ groups, together with the nitrogen through which they are attached, form a heterocyclic ring of 4 to 6 ring atoms, where one carbon may be optionally replaced with N, O, S, or $SO_2$, and where any carbon ring atom or additional N atom may be optionally substituted with $C_1$ to $C_4$ alkyl, F, or $CF_3$;

$R_7$ is H, $C_1$ to $C_6$ alkyl, alkenyl, alkynyl, $C_3$ to $C_6$ cycloalkyl, aryl substituted with 0 to 3 $R_1$, or heteroaryl substituted with 0 to 3 $R_1$;

$R_8$ is H or $C_1$ to $C_4$ alkyl;

$R_9$ is H, F, or $C_1$ to $C_4$ alkyl;

$R_{10}$ is, independently at each occurrence, H, or $C_1$ to $C_4$ alkyl; or $R_{10}$ and $R_4$, together with the nitrogen to which $R_4$ is attached, form a nitrogen-containing ring containing 3 to 6 carbon atoms;

n is an integer from 0 to 4;

m is an integer from 1 to 2;

$R_{11}$ is alkyl, alkoxy, halo, $CF_3$, $OCF_3$, hydroxy, alkanoyloxy, nitro, cyano, alkenyl, alkynyl, alkylsulfoxide, alkylsulfone, alkylsulfonamide, or alkylamido; or two adjacent $R_{11}$ also represent methylenedioxy;

wherein 1 to 3 carbon atoms in ring A may optionally be replaced with N; and wherein the dotted line between the two $R_4$ groups represents an optional heterocyclic ring of 4 to 6 ring atoms that may be formed between the two $R_4$ groups, together with the nitrogen through which they are attached.

2. A compound according to claim 1, wherein:
$R_3$ is H, F, $C_1$ to $C_4$ alkyl.

3. A compound according to claim 1, wherein:
$R_1$ is, independently at each occurrence, $R_1$ is alkyl, alkoxy, halo, $CF_3$, $OCF_3$, aryl, heteroaryl, hydroxy, alkanoyloxy, nitro, and cyano.

4. A compound according to claim 1, wherein:
$R_2$ is aryl substituted with 0 to 3 $R_1$.

5. A compound according to claim 1, wherein:
$R_2$ is phenyl, naphthyl, chloro-substituted phenyl, fluoro-substituted phenyl, or chloro, fluoro-substituted phenyl.

6. A compound according to claim 1, wherein:
$R_2$ is heteroaryl substituted with 0 to 3 $R_1$.

7. A compound according to claim 1, wherein:
$R_3$ is $OR_{12}$.

8. A compound according to claim 1, wherein:
$R_4$ is, independently at each occurrence, H, $C_1$ to $C_4$ alkyl, arylalkyl, heteroarylmethyl, cycloheptylmethyl, cyclohexylmethyl, cyclopentylmethyl, or cyclobutylmethyl.

9. A compound according to claim 1, wherein:
$R_4$ is, independenly at each occurrence, H or $C_1$ to $C_4$ alkyl.

10. A compound according to claim 1, wherein:
$R_7$ is H, $C_1$ to $C_6$ alkyl, alkenyl, alkynyl, $C_3$ to $C_6$ cycloalkyl, aryl substituted with $R_1$, or heteroaryl substituted with $R_1$.

11. A compound according to claim 1, wherein:
$R_7$ is H, $C_1$ to $C_4$ alkyl, or substituted phenyl.

12. A compound according to claim 1, wherein:
$R_8$ is H, methyl, or ethyl.

13. A compound according to claim 1, wherein:
$R_9$ is H, methyl, or ethyl.

14. A compound according to claim 1, wherein:
$R_{10}$ is H, methyl, or ethyl.

15. A compound according to claim 1, wherein:
n is an integer from 0 to 2.

16. A compound according to claim 1, wherein:
n is an integer from 0 to 1.

17. A compound according to claim 1 wherein:
n is 0.

18. A compound according to claim 1 wherein:
m is 1.

19. A compound according to claim 1, wherein:
$R_{11}$ is alkyl, alkoxy, halo, $CF_3$, $OCF_3$, hydroxy, alkanoyloxy, nitro, or cyano.

20. A compound according to claim 1, wherein:
Z is $NR_7$;
$R_7$ is $C_1$ to $C_4$ alkyl, or aryl substituted with 0 to 2 $R_1$;
$R_1$ is, independently at each occurrence, methyl, methoxy, hydroxy, halo, CN, $CF_3$, or $OCF_3$,
$R_2$ is aryl substituted with 0 to 2 $R_1$, or heteroaryl substituted with 0 to 2 $R_1$;
$R_3$ is H or OH;
one of $R_4$ is methyl and the other $R_4$ is H;
$R_8$ is H;
$R_9$ is H;
$R_{10}$ is H;
m is 1;
n is 0 to 2 and
no carbon atoms in the ring A are replaced with N.

21. A compound according to claim 1, wherein said compound is:
3-[3-(4-chlorophenyl)-2,2-dioxido-2,1,3-benzothiadiazol-1(3H)-yl]-N-methyl-3-phenylpropan-1-amine;
3-(3-chloro-5-fluorophenyl)-3-(3-isopropyl-2,2-dioxido-2,1,3-benzothiadiazol-1(3H)-yl)-N-methylpropan-1-amine;
3-(3-chloro-5-fluorophenyl)-N-methyl-3-(3-methyl-2,2-dioxido-2,1,3-benzothiadiazol-1(3H)-yl)propan-1-amine;
N-methyl-3-(3-methyl-2,2-dioxido-2,1,3-benzo thiadiazol-1(3H)-yl)-3-phenylpropan-1-amine;
N-methyl-3-(3-methyl-2,2-dioxido-2,1,3-benzothiadiazol-1(3H)-yl)-3-phenylpropan-1-amine;
3-(3-isopropyl-2,2-dioxido-2,1,3-benzothiadiazol-1(3H)-yl)-N-methyl-3-phenylpropan-1-amine;
3-(3-fluorophenyl)-3-(3-isopropyl-2,2-dioxido-2,1,3-benzothiadbzol-1(3H)-yl) -N-methylpropan-1-amine; or
a pharmaceutically acceptable salt thereof.

22. A compound according to claim 1, wherein said compound is:
(3R)-3-[3-(4-chlorophenyl)-2,2-dioxido-2,1,3-benzothiadiazol- 1(3H)-yl]-N-methyl-3-phenylpropan-1-amine;
(3R)-3-(3-chloro-5-fluorophenyl)-3-(3-isopropyl-2,2-dioxido-2,1,3-benzothiadiazol-1(3H)-yl)-N-methylpropan-1-amine hydrochloride;
(3R)-3-(3-chloro-5-fluorophenyl)-N-methyl-3-(3-methyl-2,2-dioxido-2,1,3-benzothiadiazol-1(3H)-yl)propan-1-amine hydrochloride;
(3R)-N-methyl-3-(3-methyl-2,2-dioxido-2,1,3-benzo thiadiazol-1(3H)-yl)-3-phenylpropan-1-amine hydrochloride;
(3S)-N-methyl-3-(3-methyl-2,2-dioxido-2,1,3-benzothiadiazol-1(3H)-yl)-3-phenylpropan-1-amine hydrochloride;
(3R)-3-(3-isopropyl-2,2-dioxido-2,1,3-benzothiadiazol-1 (3H)-yl)-N-methyl-3-phenylpropan-1-amine;
(3R)-3-(3-fluorophenyl)-3-(3-isopropyl-2,2-dioxido-2,1, 3-benzothiadiazol -1(3H)-yl)-N-methylpropan-1-amine hydrochloride; or
a pharmaceutically acceptable salt thereof.

23. A composition, comprising:
a. at least one compound according to claim 1; and
b. at least one pharmaceutically acceptable carrier.

24. A method for treating a condition ameliorated by inhibition of norepinephrine reuptake selected from the group consisting of vasomotor symptoms, depression disorder, pain and a combination thereof, in a subject in need thereof, comprising the step of:
administering to said subject an effective amount of a compound according to claim 1 or pharmaceutically acceptable salt thereof.

25. A method for treating at least one vasomotor symptom in a subject in need thereof, comprising the step of:
administering to said subject an effective amount of a compound according to claim 1 or pharmaceutically acceptable salt thereof.

26. A method according to claim 25,
wherein said vasomotor symptom is hot flush.

27. A method according to claim 26,
wherein said subject is a human female.

28. A method according to claim 27,
wherein said human female is pre-menopausal.

29. A method according to claim 27,
wherein said human female is peri-menopausal.

30. A method according to claim 27,
wherein said human female is post-menopausal.

31. A method according to claim 26,
wherein said subject is a male.

32. A method according to claim 31,
wherein said human male is naturally, chemically or surgically andropausal.

33. A method for treating at least one depression disorder in a subject in need thereof, comprising the step of:
administering to said subject an effective amount of a compound according to claim 1 or pharmaceutically acceptable salt thereof.

34. A method according to claim 33,
wherein said depression disorder is major depressive disorder, anxiety, sleep disturbance, or social phobia.

35. A method for treating pain in a subject in need thereof, comprising the step of:
administering to said subject an effective amount of a compound according to claim 1 or pharmaceutically acceptable salt thereof.

36. A method according to claim 35,
wherein said pain is acute centralized pain, acute peripheral pain, or a combination thereof.

37. A method according to claim 35,
wherein said pain is chronic centralized pain, chronic peripheral pain, or a combination thereof.

38. A method according to claim 35,
wherein said pain is neuropathic pain, visceral pain, musculoskeletal pain, bony pain, cancer pain, inflammatory pain, or a combination thereof.

39. A method according to claim 38,
wherein said neuropathic pain is associated with diabetes, post traumatic pain of amputation, lower back pain, cancer, chemical injury, toxins, major surgery, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, viral infection, bacterial infection, metastatic infiltration, adiposis dolorosa, burns, central pain conditions related to thalamic conditions, and combinations thereof.

40. A method according to claim 38,
wherein said visceral pain is associated with ulcerative colitis, irritable bowel syndrome, irritable bladder, Crohn's disease, rheumatologic (arthralgias), tumors, gastritis, pancreatitis, infections of the organs, biliary tract disorders, and combinations thereof.

41. A method according to claim 35,
wherein said pain is female-specific pain.

* * * * *